US012667292B2

(12) United States Patent　(10) Patent No.: US 12,667,292 B2
Koczan　(45) Date of Patent: Jun. 30, 2026

(54) RADAR DEVICE FOR TOILETS

(71) Applicant: Withings, Issy les Moulineaux (FR)

(72) Inventor: Xavier Koczan, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 293 days.

(21) Appl. No.: 18/475,789

(22) Filed: Sep. 27, 2023

(65) Prior Publication Data

US 2024/0108267 A1　Apr. 4, 2024

(30) Foreign Application Priority Data

Oct. 3, 2022　(FR) ...................................... 2210069

(51) Int. Cl.
| | |
|---|---|
| *A61B 5/20* | (2006.01) |
| *A61B 5/00* | (2006.01) |
| *G01N 33/493* | (2006.01) |
| *G01S 13/34* | (2006.01) |
| *G01S 13/58* | (2006.01) |

(52) U.S. Cl.
CPC ............ *A61B 5/208* (2013.01); *A61B 5/6887* (2013.01); *G01N 33/493* (2013.01); *G01S 13/34* (2013.01); *G01S 13/583* (2013.01)

(58) Field of Classification Search
CPC ....... A61B 5/208; A61B 5/6887; A61B 5/207; G01S 13/34; G01S 7/415
See application file for complete search history.

(56) References Cited

U.S. PATENT DOCUMENTS

| | | | | |
|---|---|---|---|---|
| 9,671,343 B1 * | 6/2017 | Hall | ......................... | E03D 11/11 |
| 11,604,177 B1 * | 3/2023 | Park | .......................... | G06T 7/90 |
| 2017/0105670 A1 * | 4/2017 | Holt | ...................... | G01F 23/263 |
| 2020/0268303 A1 | 8/2020 | Oliva | | |

FOREIGN PATENT DOCUMENTS

| | | |
|---|---|---|
| FR | 3 119 977 A1 | 8/2022 |
| FR | 3 126 611 A1 | 3/2023 |
| FR | 3 126 612 A1 | 3/2023 |
| FR | 3 126 613 A1 | 3/2023 |
| FR | 3 126 614 A1 | 3/2023 |

(Continued)

OTHER PUBLICATIONS

"Antenna Design of Millimeter Wave Radar for Smart Toilet" by Y. Yang et al. 13th Int. Symp. Anten. Prop. EM ISAPE. 2021.*

(Continued)

*Primary Examiner* — Jason M Ip

(74) *Attorney, Agent, or Firm* — CUSHMAN PARTNERS, LLC

(57) ABSTRACT

A measurement method of a urine stream of a user during urination to identify a user, the measuring method using a radar sensor and including emitting, by the radar sensor, at least one radar signal in a direction of the urine stream, receiving, by the radar sensor, a reflected radar signal, the received radar signal including reflections of the emitted signal, the reflections being caused by at least the urine stream, processing, the received radar signal, to determine at least one property relating to the urine stream, and assigning the urine stream to one of a plurality of user profiles on the basis of the at least one property of the urine stream.

19 Claims, 12 Drawing Sheets

(56)                 References Cited

FOREIGN PATENT DOCUMENTS

| | | | |
|---|---|---|---|
| JP | 2009-036585 | A | 2/2009 |
| WO | WO 2021/055681 | A1 | 3/2021 |
| WO | WO 2021/175909 | A2 | 9/2021 |
| WO | WO 2021/175944 | A1 | 9/2021 |

OTHER PUBLICATIONS

"Age, gender, and voided vol. dependency of peak urinary flow rate . . . " by V. Kumar et al. Indian J Urology. 2009.*

Park, S.-M., et al., "A mountable toilet system for personalized health monitoring via the analysis of excreta," Nature Biomedical engineering, Apr. 2020, 14 pages, (DOI: 10.1038/s41551-020-0562-5).

* cited by examiner

602

604

1000

RADAR DEVICE FOR TOILETS

CROSS-REFERENCE TO RELATED APPLICATIONS

This application claims priority to French Patent Application No. FR2210069, filed Oct. 3, 2022, the entire content of which is incorporated herein by reference in its entirety.

FIELD

The present description relates to devices and methods for identifying a toilet user. Such identification is particularly useful in the context of urinalysis tests, where it may be desirable to be able to identify the urinator in order to attribute the results of the urinalysis to the right person, or to trigger a urinalysis measure.

Urinalysis is nowadays mainly carried out in specialized laboratories, or in a rather rudimentary way at home. In both cases, the active intervention of a person is required, whether a laboratory technician or the user him/herself, in order to carry out the urine sampling: identification of the user poses no technical difficulty.

The present description also relates to the analysis of a urine stream by non-invasive methods.

BACKGROUND

Technical developments are making automated testing possible at home. By automated, we mean that the user's actions are reduced to a minimum. For example, documents WO2021/175909, WO2021/175944 and FR2101762 describe a stand-alone urine device to be positioned in the toilet at the user's home. One of the problems associated with this type of device, which automatically collects urine and analyzes it, is attributing the measurement to a specific urinating user among a plurality of potential users. There is therefore a need to be able to identify the user. The above-mentioned documents describe a number of possible approaches, such as interaction with a button or Bluetooth recognition. The document "*A mountable toilet system for personalized health monitoring via the analysis of excreta*", Park et al, in *Nature Biomedical engineering* (DOI: 10.1038/s41551-020-0562-5), proposes several means, such as a fingerprint or analprint identification module.

These existing techniques have their drawbacks: the need to have a phone, the need to install a button, hygiene, invasion of privacy, the need for interaction, etc.

It is desirable to have an identification system that does not have the above-mentioned disadvantages.

SUMMARY

An aspect of the present description is to propose a method and associated devices or systems that do not present at least one of the aforementioned difficulties. More specifically, the present description proposes to use radar to identify a toilet user. In particular, urine analyses may be part of gendered analyses, in the sense that indifferent analysis of male or female urine is not necessarily relevant. Consequently, identification may, in the context of the description, mean identifying the user's biological sex.

Aspects of the invention are defined in the claims.

In an embodiment, the description presents a measurement method relating to a stream of urine from a user during urination, the measurement method using a radar sensor and comprising at least the following steps:

emission by the radar sensor of at least one radar signal, in the direction of the urine stream, reception by the radar sensor of a reflected radar signal, the received radar signal comprising reflections of the transmitted signal, the reflections being caused by at least the urine stream, processing the received radar signal to determine at least one property relating to the urine stream.

In particular, the radar sensor is installed on the wall of a toilet bowl.

The urine stream property may include at least one distance of interest between the radar sensor and the urine stream, for example the distance between the origin of the urine stream and the radar sensor.

In an embodiment, the distance of interest is obtained by:

identifying a radial velocity of interest linked to the maximum radial velocity (Vmax) of a urine front, obtaining the radial distance (Rmax) corresponding to this velocity of interest, the radial distance (Rmax) corresponding to the distance of interest.

In an embodiment, the urine stream property comprises a dispersion level (NPix) of the urine stream. In particular, the dispersion level is obtained by calculating a reflection level of the reflected radar signals.

In an embodiment, the urine stream property comprises at least one urine stream velocity of interest. The velocity of interest of the urine stream may comprise the maximum measured velocity (Vmax) of the urine stream.

The measurement method may further comprise assigning the urine stream to one of a plurality of user profiles using the at least one property of the urine stream. The assignment may comprise an assignment between a user profile associated with a male and a user profile associated with a female.

In an embodiment, classification is based on maximum measured velocity and dispersion level and/or a combination of several properties of the urine stream, including maximum measured velocity of the urine stream.

In an embodiment, the assignment is made by classification on the basis of at least one property relating to the urine stream and a classification function. The classification function may be obtained beforehand from a data set (in particular for training the classifier).

In an embodiment, the radar sensor operates per frame, each frame being generated by a plurality of chirps, and transmission and reception steps being implemented for each chirp.

In particular, the radar sensor is a Frequency Modulated Continuous Wave (FMCW) radar sensor, or the radar signal is FMCW. Radar sensor frequencies may vary between 58 GHz and 63 GHz.

Signal processing may include calculation of at least one range-doppler response, for example a distance-doppler map.

In an embodiment, the measurement method comprises a preliminary step, using a urine detector, of determining the presence of a urine stream.

The description also presents a radar device comprising a radar sensor suitable for implementing a method as precisely described.

The description also presents a radar device comprising:

a housing, suitable for positioning on an internal wall of a toilet bowl, a radar sensor, housed in the casing, suitable for emitting radar waves in the direction of the toilet bowl opening, The radar sensor may be a Frequency Modulated Continuous Wave (FMCW) radar sensor.

The radar device may include a urine detector capable of detecting a stream of urine, the urine detector being configured to activate the radar sensor in response to a detection of the stream of urine.

The description also relates to a urine analysis device, comprising:

a radar device as described above, a collection port on the housing for receiving urine, a test set for analyzing the urine received.

The radar device may include a battery to supply power to the radar sensor(s).

In particular, the housing may be waterproof.

Finally, the description relates to a non-transitory computer-readable medium including a computer program comprising instructions suitable for implementing a method as previously described when the instructions are executed by a processor. This computer program may be implemented by the radar device as described above.

In particular, a strong constraint to identification is linked to the energy management of the urine analysis device into which the radar may be integrated: the radar sensor needs to be activated as little as possible. As a result, sending forward-looking radar waves is not very feasible, since to detect seated standing movement, the radar sensor has to be activated before the user appears in the radar's field of view. To do this, either the radar sensor sends prospective radar waves, or the radar sensor is informed of the arrival of a user (but this solution makes the implementation even more complex). The solution proposed here enables optimized battery operation.

BRIEF DESCRIPTION OF THE DRAWINGS

The following figures are provided to facilitate understanding of the invention.

DETAILED DESCRIPTION

Figure 1:
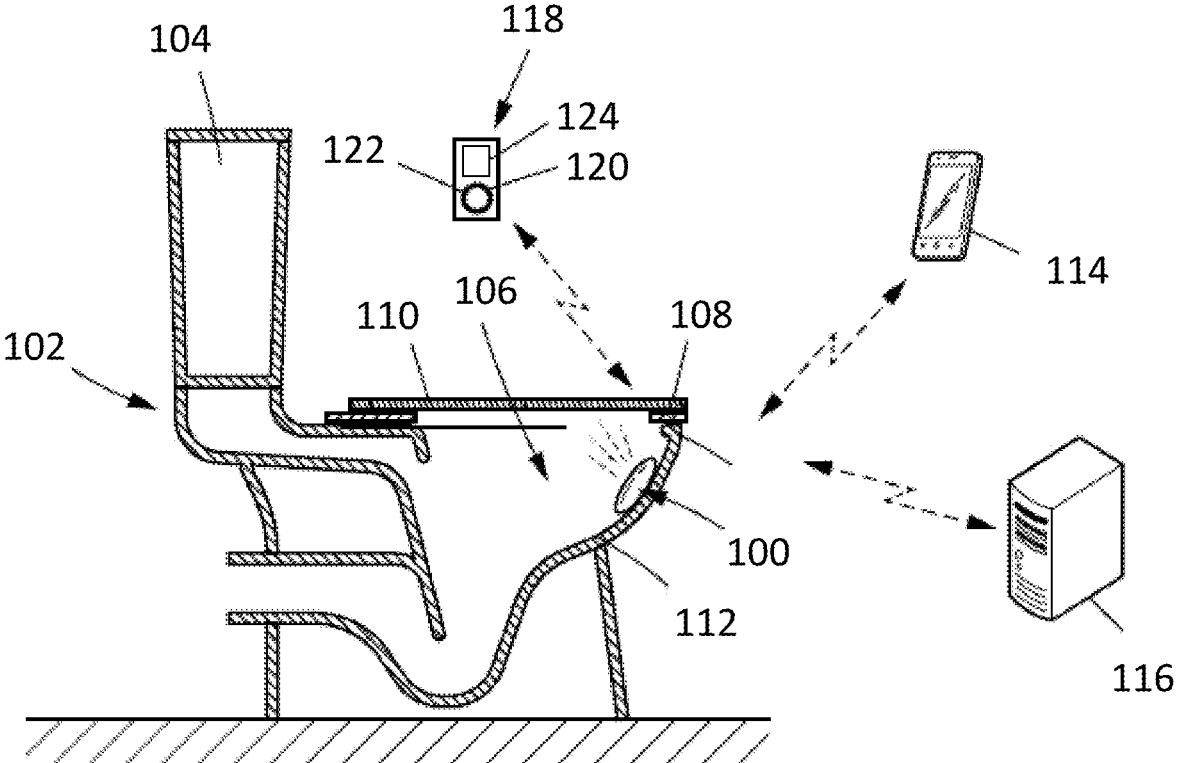
FIG. 1 schematically presents a cross-sectional view of a toilet equipped with a radar device according to an embodiment of the description.

FIG. 1 schematically illustrates a radar device 100 mounted on a toilet 102. The radar device forms an identification device. The toilet 102 comprises a water tank 104, a bowl 106, a seat 108 and a lid 110. The identification device 100 may be mounted on an inner wall 112 of the toilet bowl 106. Beneficially, the radar device 100 is entirely housed in the toilet bowl, making it unobtrusive.

In an embodiment, the radar device 100 may be positioned in the toilet so as to be in the path of a stream of urine secreted by a user during urination, in particular when a user urinates in a seated position in the toilet. The position of the urine analysis device in the toilet is then suitable for any type of user, male or female, regardless of age. The user may then urinate in the toilet without having to worry about the position of the urinal.

The positioning of radar device 100 also enables it to be positioned in the path of a flush from cistern 104. This allows the identification device 100 to be flushed when the toilet is flushed.

An attachment may be provided to hold the radar device 100 to the inner wall of the bowl: suction cup, magnet (with support glued to the wall), hook reaching the rim of the bowl, etc.

The radar device 100 may communicate with a mobile terminal 114 (such as a smartphone) and/or an external server 116. In an embodiment, the radar device 100 communicates with the mobile terminal 114 (e.g. directly via BLUETOOTH® (a short-range wireless technology standard such as BLUETOOTH® Low Energy) and the mobile terminal 114 communicates with the server 116 (via a cellular or WiFi connection). In another embodiment, the radar device 100 may communicate directly with the server 116 via a cellular network.

Figure 2:
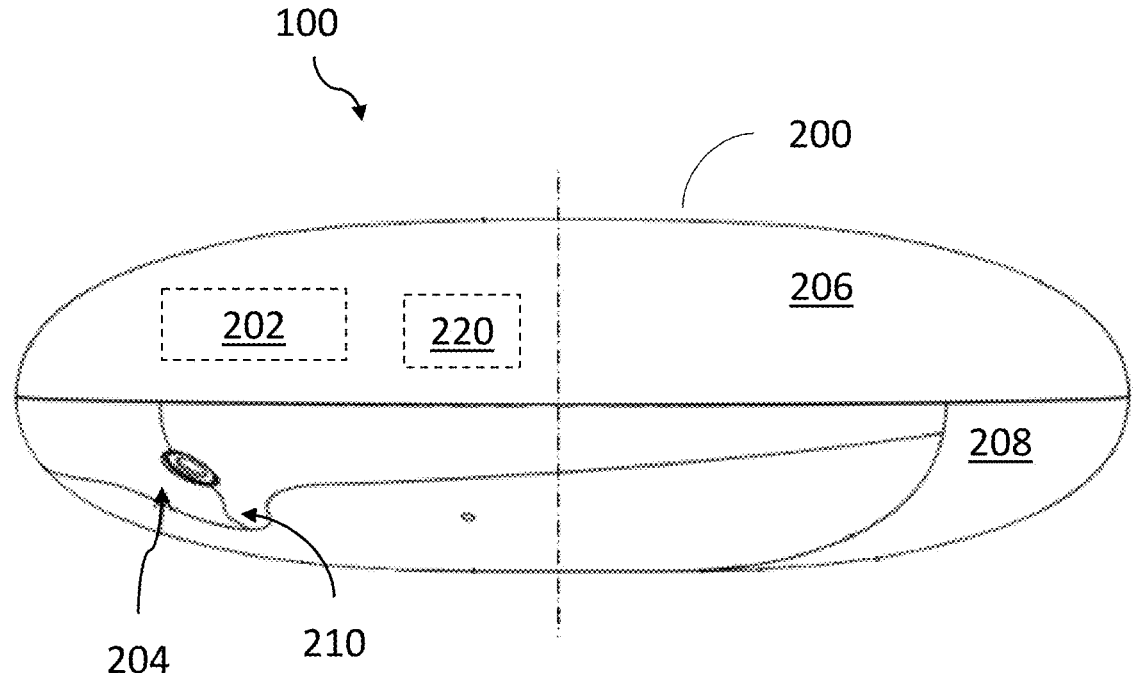
FIG. 2 shows a more detailed view of a housing of a radar device associated with a urine analysis device, according to an embodiment of the description.

With reference to FIG. 2, the radar device 100 may comprise a housing 200 inside which a radar sensor 202 is positioned (shown schematically as a dotted line). The housing 200 is dimensioned so that it may be positioned in the toilet bowl 106 of the toilet 102. Because it is positioned in a region exposed to various liquids or solids, the 200 housing is watertight. In an embodiment, the housing 200 comprises a collection orifice 204, suitable for receiving urine dripping onto the housing 200. In this embodiment, the radar device 100 is part of a urine analysis device which includes the housing 200. The housing 200 may comprise a front shell 206 and a rear shell 208, which may be assembled and disassembled for access to the interior of the housing 200. The urine analysis device has been described in documents WO2021/175909, WO2021/175944 (publication numbers), FR2109383, FR2109384, FR2109391, and FR2109392 (application numbers). The contents of all of these documents are incorporated herein by reference in their entireties.

Figure 3:
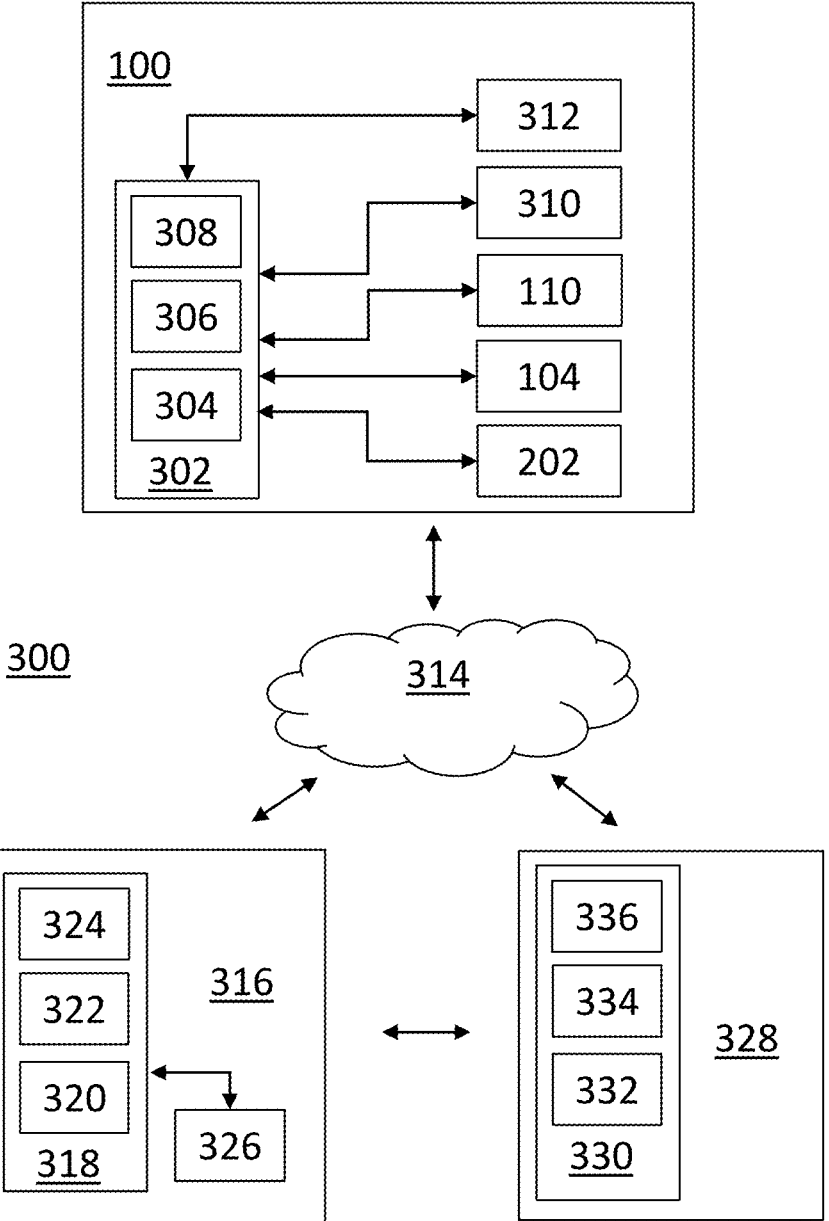
FIG. 3 shows schematically a view of the components of a radar device according to an embodiment of the description, as well as its ecosystem.

FIG. 3 shows, in a 300 diagram, the components that may be included in the radar device 100, and the general ecosystem. The radar device 100 comprises a control circuit 302 with a processor 304, a memory 306 and an I/O (input/output) interface 308 configured to send and receive data from the control circuit 302. A communication module 310 may be provided for exchanging data with an external terminal (e.g. a smartphone). The communication module 310 may be a wireless module, such as Wi-Fi, BLU- ETOOTH®, BLUETOOTH® Low Emission, etc. In particular, the control circuitry 302 may exchange with the radar sensor 202 to send acquisition instructions and receive radar data to be processed.

The radar device 100 may include a battery 312 that supplies power to the components.

Memory 306 may store instructions which, when executed by processor 304, implement the method(s) and or function(s) of the present description. In an embodiment, the methods are carried out locally, by the processor 304 of the radar device 100, enabling the user to return to the device without the need for a connection to the external terminal (smartphone).

The radar device 100 may communicate, using the communication module 310 and a communication network 314, with an external mobile terminal 316, such as a smartphone. The mobile terminal 316 comprises control circuitry 318 with a processor 320, a memory 322 and an I/O interface 324 configured to send and receive data from the control circuitry 302. The external terminal 316 further comprises a user interface 326 for interacting with the user. The processor 320 and memory 322 may implement an application that enables the external terminal 316 to communicate with the measuring device 100. In particular, the user interface 326 may display information to the user.

The radar device 100 may also communicate with a server 328, either directly via the communication network 314 or via the external terminal 316. Server 328 comprises control circuitry 330 with a processor 332, memory 334 and an I/O interface 336 configured to send and receive data from control circuitry 302. Server 328 may store measurements made by radar device 100 (cloud architecture). Server 328 may also perform data processing.

The communication network 314 may be heterogeneous: short-range wireless (BLUETOOTH®, Wi-Fi, etc.), long-range wireless (cellular, etc.), wired (Ethernet, etc.).

Figure 4:
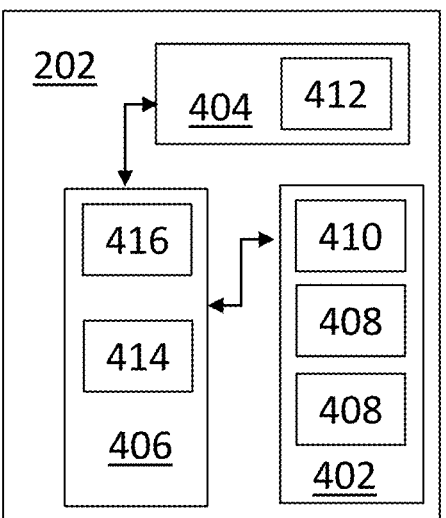
FIG. 4 shows schematically a more detailed view of a housing of a radar device associated with a urine analysis device, according to an embodiment of the description.

FIG. 4 describes an example of a radar sensor 202 in more detail. The radar sensor 202 comprises a transmitter 402, a receiver 404 and control circuitry 406. Transmitter 402 comprises at least one transmit antenna Tx 408 and a wave generator 410. Receiver 404 comprises at least one Rx receiver antenna 412. The control circuitry 406 includes a processor 414 and a memory 416, to control the transmitter 402 and process the signals received by the receiver 404. The control circuitry 406 of the radar sensor 202 may be integrated or partially integrated with the control circuitry 302 of the radar device 100 and will hereinafter be referred to as "control circuitry 302, 406". In particular, the radar sensor 202 uses the Doppler-Fizeau effect generated by a moving object to obtain the speed of the object and/or the distance between the object and the radar sensor 202. The velocity is referred to as radial, as it is only the velocity component projected onto an axis connecting the object and the radar sensor 202. Similarly, the distance is referred to as radial, as it is the distance along this axis.

The wave generator 410 and the Tx antenna generate electromagnetic waves, emitted in the direction of a FoV ("field of view"). These electromagnetic waves are partially reflected by the obstacles they encounter, creating an echo that is received by the Rx antenna 404. Control circuitry 302, 406 processes the echoes to generate radar data. The control circuitry 302, 406 may convert the analog signals generated by the wave generator 310 and received by the Rx antenna into digital signals. Filters, amplifiers, etc. are typically provided in the radar sensor 202.

The radar sensor 202 may be compact, of the order of a few centimeters, or even less than 1 cm. For example, radar sensor 202 may be contained in a cube measuring 1 cm×1 cm×1 cm.

The FoV field of view is typically a solid angle, covering a volume of space from the 202 radar sensor. The FoV is typically defined by two aperture angles. The axis of symmetry of each angle is called the radar axis.

Figure 5:
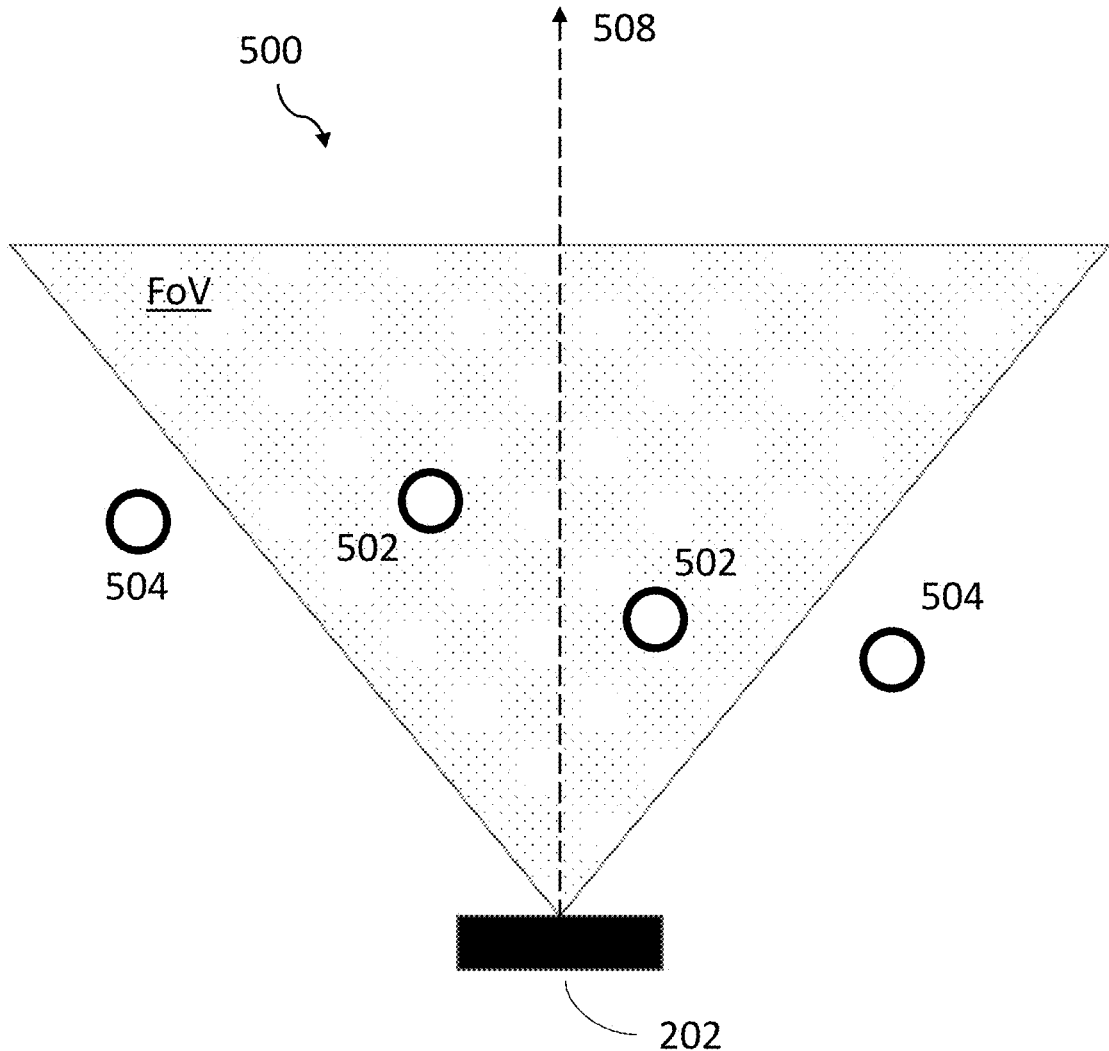
FIG. 5 shows several situations representing the origin of the urine jet and its direction, relative to the FoV ("field of view") of the radar sensor.

With reference to FIG. 5, the radar sensor 202 may be a frequency-modulated continuous wave (FMCW) radar, which means that the radar sensor emits a frequency-modulated signal ("chirp" in the accepted terminology). In other words, during a pulse of duration T, the frequency of the chirp emitted varies over a range. Several modulations are possible: sawtooth modulation, triangular modulation, frequency shift keying, staircase modulation, etc. Ultra Wide Band (UWB) radar may also be used as a radar sensor. The UWB radar emits wave patterns of a few nanoseconds which are repeated. The study of delays enables distances to be determined, and the study of delay variations enables speeds to be determined.

The radar sensor 202 may emit a succession of chirps, the succession being called a "frame". In an embodiment, a frame comprises between 16 and 256 chirps, or even between 32 and 64 chirps (e.g. 128 chirps). More specifically, a frame may be broken down as follows: $N \cdot (PRT) = N \cdot (t\_chirp + t\_pause)$, where PRT is the pulse repetition time, where t_chirp is the time of a chirp, t_pause is the pause time before the next chirp and N is the number of chirps. The PRT may last between 300 μs and 500 μs. The pause may be 100 μs. A frame may thus last a few milliseconds.

Figure 6:
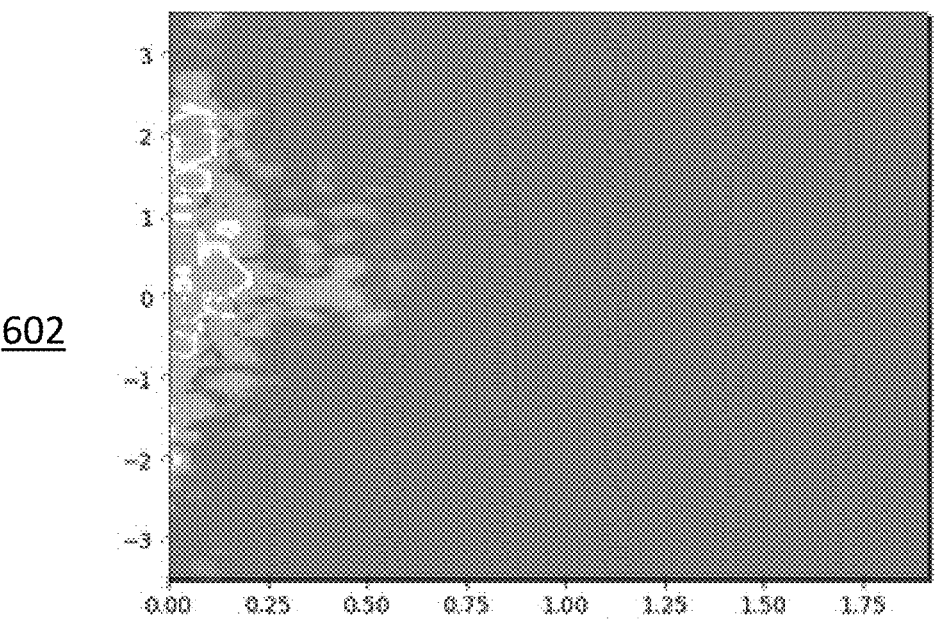
FIG. 6 shows two "distance-doppler" maps, for a male person and a female person, according to an embodiment of the description.
Figure 6:
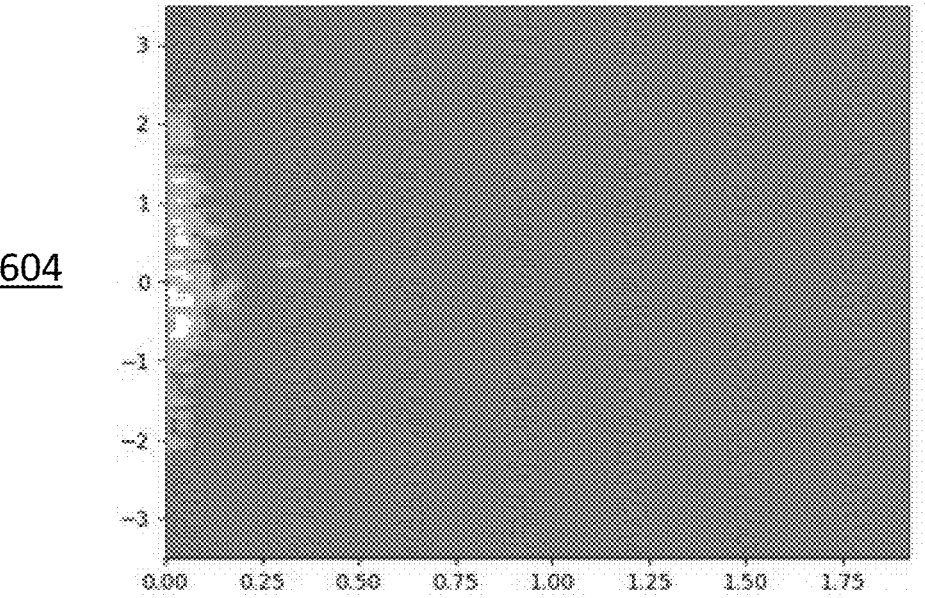

After mixing the transmitted and received signals, filtering, etc., frequency modulation creates a signal known as the "Intermediate Frequency Signal", whose frequencies are proportional to the distance of the objects causing the echoes. A Fourier transform applied to this intermediate frequency signal highlights the frequencies and associated distances. By analyzing the phase variations of the Fourier transforms on successive chirps, we can highlight the Doppler frequencies, which are linked to the object's speed. The radar sensor 202 may obtain speed and distance for each object. In particular, the radar sensor 202 may generate a "Range-Doppler" map, which represents the distance (on the abscissa figures, in m) and speed of a moving object in the FoV field of view (on the ordinate figures, in m/s), as shown in FIG. 6. For each frame, a "Distance-Doppler" map may be calculated.

In frames, the "Distance-Doppler" map is obtained using FFTs (fast fourier transforms) and their evolution between successive chirps. Distance-Doppler" maps are well known and will not be described in greater detail here.

Using chirps in particular, the 202 radar sensor may also calculate a distance between itself and a moving object.

A frame may last 100 ms. Therefore, twenty successive frames take 2 s. More generally, in the case of FMCW radar, a chirp may last between 100 and 200 ms.

In the examples shown in the description, radar sensor 202 is an Infineon BGT60TR13C FMCW radar whose frequency may vary between 58 GHz and 63.5 GHz during a chirp. This range allows a bandwidth of more than 5 GHz, which ensures sufficient accuracy for the application described. Other frequency values may be used, in particular around the values described. This radar sensor comprises three Rx antennas and one Tx antenna. In the example shown, the chirp comprises sawtooth frequency modulation.

To improve signal quality and to better capture wave reflections in the toilet, the radar device 100 is positioned in the toilet so that the field of view FoV of the radar sensor 202 is oriented towards the toilet opening, meaning that a user sitting on the seat 108 is in radar coverage and in particular the user's posterior, the user's genitals and the urethra outlet, which is the origin of the user's urine stream.

Because of the anatomical differences between a male person and a female person, the position of the origin of the urine stream is not the same when the user is seated on seat 108. In addition, the urine stream is different between a male person and a female person for various morphological reasons (shape of the urethra, pressure, flow rate, etc.).

In an embodiment, the radar device 100, by means of one or more frames, may identify properties of the urine stream, these properties making it possible in particular to classify the urine stream as belonging to a given user. The classification of a user may be at least a classification by discrimination between the biological sex of the user: male and female. In a household, where the only users of the radar device 100 are a male person and a female person, this anatomical discrimination based on biological sex makes it possible to identify the user of the radar device 100.

Because of anatomical differences between males and females, variations in the placement of each radar device 100 and the shapes of toilet bowls, several situations may arise during seated urination. These situations are shown in FIG. 5, which illustrates four configurations 500, 502, 504, 506 in two dimensions, with radar sensor 202, radar axis 508, field of view FoV and the position of the origin (the circle) of the urine stream and the overall direction (the dotted arrow starting from the circle) of the urine stream.

In a first case 502, the origin of the urine jet is located in the field of view FoV of the radar sensor 202: in this case, the radar sensor 202 perceives high-intensity direct reflections as well as multiple reflections from wave bounces on the bowl of lower speed and intensity.

In a second case 504, the origin of the urine jet is outside the field of view FoV of the radar sensor 202: in this case, the radar sensor 202 no longer perceives direct reflections. The signal then consists solely of multiple reflections of low intensity and low speed at greater distances. In addition, because of the arrangement of radar sensor 202, if the origin of the urine stream is outside the field of view FoV, the urine stream is likely to be of shorter length.

In the first case 502, the distance between the jet origin and the radar device 100 may be determined to identify the user. In the second case 504, the reflection level may be determined to identify the user, as will be explained in more detail later. For anatomical reasons, the second case 504 generally occurs with males.

In an embodiment, the radar sensor 202 emits a chirp and receives a reflected signal. This reflected signal is then processed by a processor (either the control circuitry 406 of the radar sensor 202, or the control circuitry 302 of the radar device 100) to generate, in particular, after transmitting a plurality of chirps and receiving the reflected signals (i.e., an image), a "distance-doppler" map. FIG. 6 shows two "distance-doppler" maps 602, 604: map 602 illustrates the results for a female user and map 604 illustrates the results for a male user. From these maps, several properties relating to the urine stream may be obtained: radial distance, radial velocity and a dispersion level.

A "distance-doppler" map may be generated from a single frame (i.e. calculated from a plurality of chirps).

As previously mentioned, a "distance-doppler" map represents the intensity of the reflected signal (which is related to the number of moving objects) as a function of the radial distance between the moving object and the radar device 100 and as a function of the radial velocity of this object. A negative speed represents an object moving away, and a positive speed represents an object moving towards us.

In the present description, the moving object is a urine front. A urine stream typically comprises a plurality of successive urine fronts. Map 602 thus illustrates radar signals that correspond to urine fronts at a greater distance than those observed on map 604, which corresponds to an anatomical difference: the orifice of the urine jet in a female person sitting on the toilet will be further away from radar sensor 202 than the orifice of the urine jet in a male person sitting on the toilet.

Map 602 also illustrates radar signals that correspond to urine fronts with greater radial velocity, which again corresponds to an anatomical difference: urine ejection velocity is greater in a female person, due to the longer male outflow tracts that generate pressure losses. Map 602 illustrates radar signals that are more dispersed than those observed on map 604, corresponding to a more fragmented plurality of objects (the urine jet and its reflections): due to the greater distance in a female person than in a male person, and the nature of the urethra, the probability of a jet hitting the bowl and being reflected is greater.

Control circuitry 302, 406 may extract these properties (radial distance, radial velocity and dispersion) using algorithms such as image analysis and pixel counting.

Various types of information can be extracted from such maps. Firstly, a single "distance-doppler" map may be used to obtain a property relating to the urine stream, which means that in a single frame, the radar device 100 may distinguish the biological sex of the urinating user. Battery consumption is thus minimized.

Speed and Vmax

An example algorithm consists of determining a velocity of interest of the urine front. For example, this velocity of interest is, or is related to, the highest positive velocity (i.e., the radial velocity in the direction of the radar sensor 202) among the velocities of the urine fronts in the "distance-doppler" map. This speed is called Vmax. This determination may be made directly on the "distance-doppler" map, in particular by identifying the urine front (including low-intensity urine fronts) with the highest radial velocity. Remember that the "distance-doppler" map already gives the radial velocities of the urine fronts.

Alternatively, an example of an algorithm is to identify an average measured velocity or other calculation from the velocity of the urine fronts.

The urine stream property is then a radial velocity of interest of urine fronts, such as a maximum measured velocity.

Radial Distance and Rmax

One example of an algorithm consists in determining the maximum distance between the radar sensor 202 and all the urine fronts. In this respect, the algorithm may identify the urine front with the highest positive velocity (i.e. the radial velocity in the direction of the radar sensor, called Vmax) and then retrieve the radial position of said urine front. This radial distance is called Rmax.

The urine front at or near the urethra is considered to be the fastest, as the radial component is the largest.

The urine stream property is then a radial distance of interest between the radar sensor 202 and the urethra outlet.

Reflection Level and Npix

An example of an algorithm is to identify the reflection level of radar waves. This reflection level is called Npix and depends on the dispersion of the urine stream. In this respect, the algorithm may count the number of fronts or the number of fronts with an intensity above a predetermined threshold. In practical terms, this is equivalent to measuring the area of non-uniform zones on the "Doppler distance" map, independently of the intensity of the object in each zone (the color).

The property relating to the urine stream is then a dispersion level of the urine stream (either during the urine stream itself, or by the reflections of the urine stream on the bowl).

Use of Urine Stream Properties

In an embodiment, properties relating to the urine stream may be used to obtain physiological information about the user. For example, the velocity of interest may be correlated with bladder pressure, pressure drop or flow rate, which in turn may be correlated with pathologies (hypertrophy, cancer, nervous disorder, etc.). For example, the reflection level may be correlated with the laminar or turbulent nature of the urine stream.

In an embodiment, properties relating to the urine stream are used to identify the author of the urine stream, i.e. the person urinating. In particular, identification may include discrimination between male and female.

Figure 7:
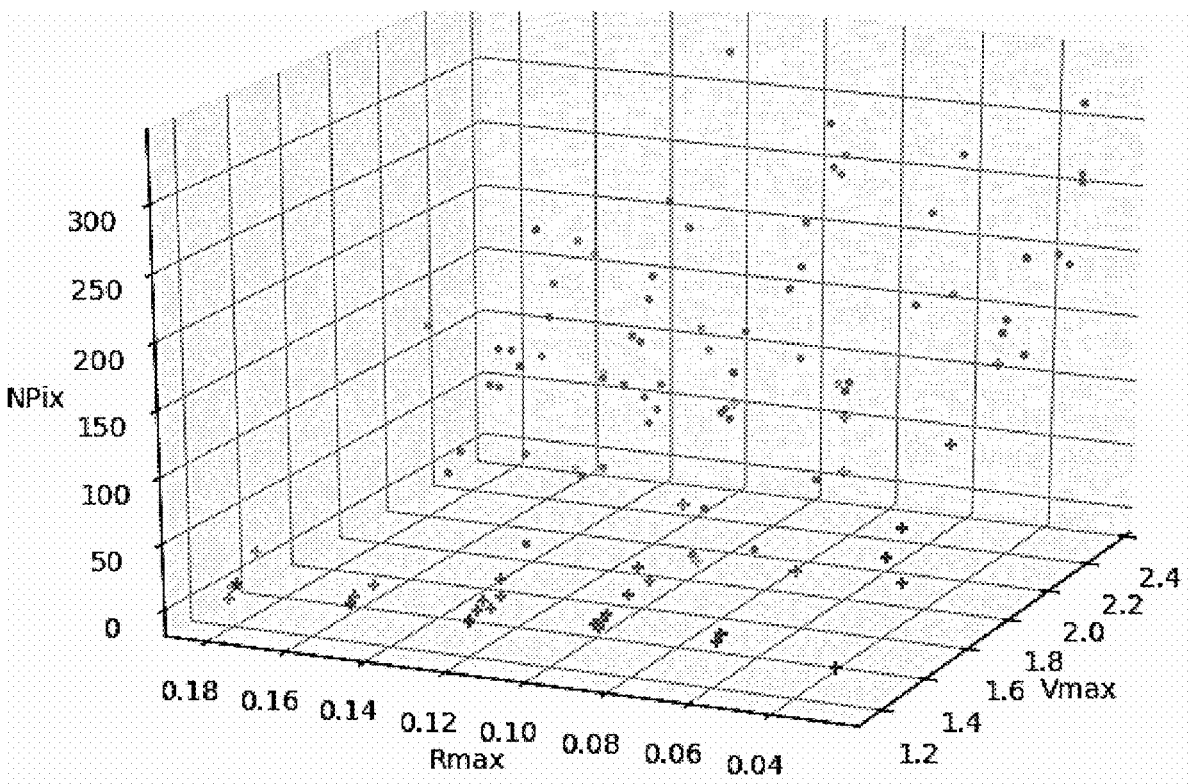
FIG. 7 shows a three-dimensional representation of urine streams using three parameters relating to the urine stream.

FIG. 7 illustrates a three-dimensional representation of a plurality of users: each point represents urination by a user, each point being placed by its Npix, Rmax and Vmax value. Points associated with male users are represented by crosses, and points associated with female users are represented by circles.

Figure 8:
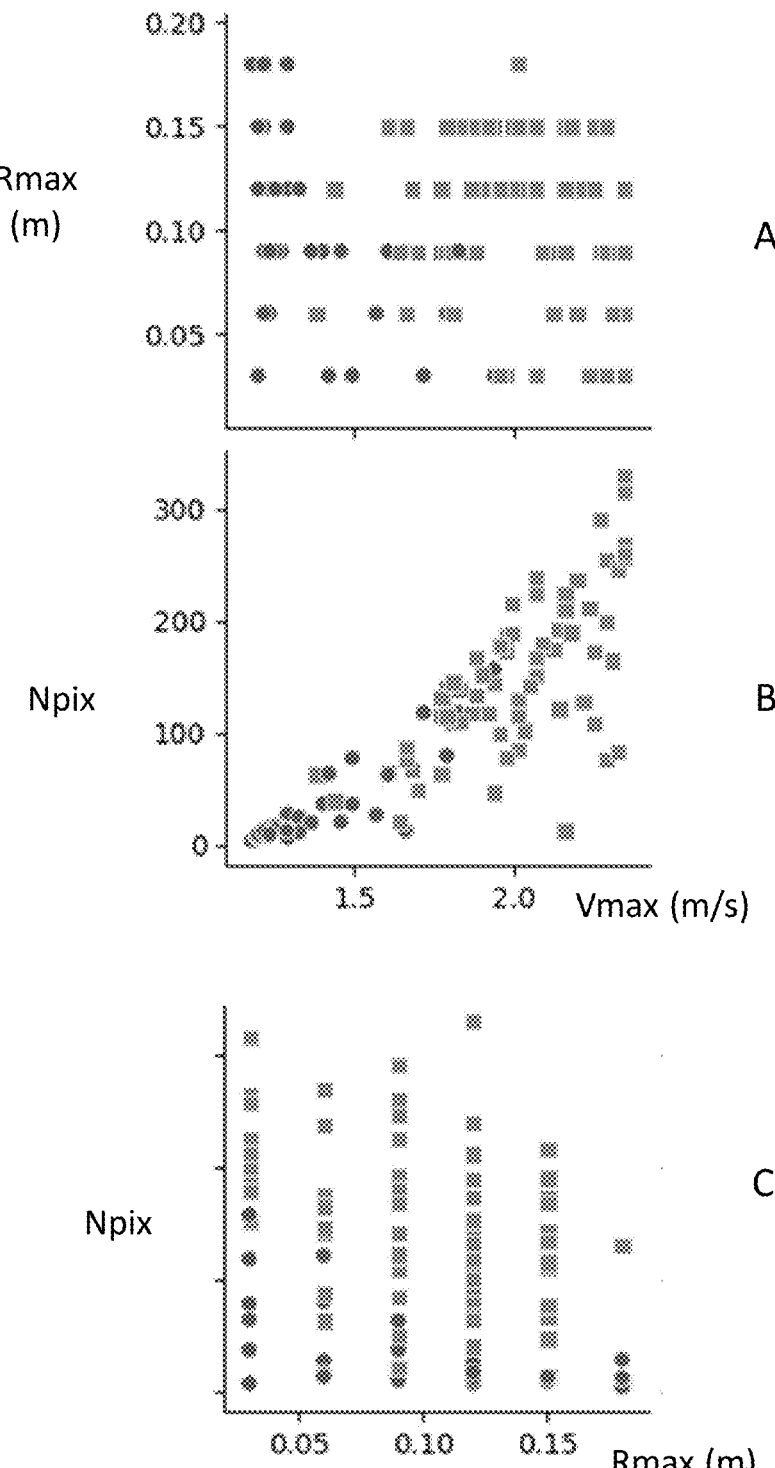
FIG. 8 shows two-dimensional graphs representing the projections of FIG. 7.

FIG. 8 shows two-dimensional projections of the above three-dimensional representation (with a different data set). In other words, we have a representation of the three properties described above (Vmax, Rmax, Npix) as a function of each other. FIG. 8 shows three graphs A, B, C. Graph A shows Rmax (in m) as a function of Vmax (in m/s); graph B shows Npix (in number) as a function of Vmax (in m/s); graph C shows Npix (in number) as a function of Rmax (in m).

These representations allow us to visually highlight proofs of concept of biological sex discrimination using at least one property obtained by the radar sensor. The squares represent female users and the circles male users. The data in FIG. 8 were obtained from an in-house campaign involving 5 males and 5 females, with at least ten micturitions each.

Male and female users are clearly identifiable on some of the projections shown.

For example, training on a labeled data set may determine male/female clusters. For example, in two-dimensional representations, training may determine a classification function F(Rmax; Vmax) that partitions the space and allows male and female clusters (or partitioning). The male/female clusters in graph C in FIG. 8 may be separated by a classification function F(NPix; Vmax) because females generally have a higher Vmax than men. For example, the classification function A·NPix+B·Vmax+C=0 defines a straight line that divides the space of (NPix; Vmax) pairs in two. A new point pair (NPix'; Vmax') will be classified as male or female according to the value of A·NPix'+BVmax', which will be either less than 0 or greater than 0. More precise F classification functions may be defined to define more restricted clusters. More generally, we speak of classification rules, obtained using labeled data.

Classification using the NPix and Vmax properties yields usable classification results.

Classification using the three properties NPix, Vmax and Rmax may further refine the results. In this case, we define a classification function F(NPix; Vmax; Rmax) that compartmentalizes the space of trouples (NPix; Vmax; Rmax).

Thanks to this algorithm, no user calibration is required.

Calculation of the properties of the urine stream may be performed by control circuitry 302, 406. Assignment of the urine stream to a particular user may be carried out by the control circuitry. Local execution makes it possible to quickly identify the user.

Example of Physical Explanations

In females, the jet is rapidly turbulent and further away from the radar sensor, creating more of a urine front and therefore a greater reflection of the radar signal, resulting in a generally higher NPix.

The radial distance Rmax is lower in males than in females, due to the position of the urethra on the 202 radar sensor. Nevertheless, in the present results, some urethras were outside the FoV of the radar sensor, making it more difficult to use Rmax for classification. In this case, however, Npix and Vmax may be used to classify.

Figure 9:
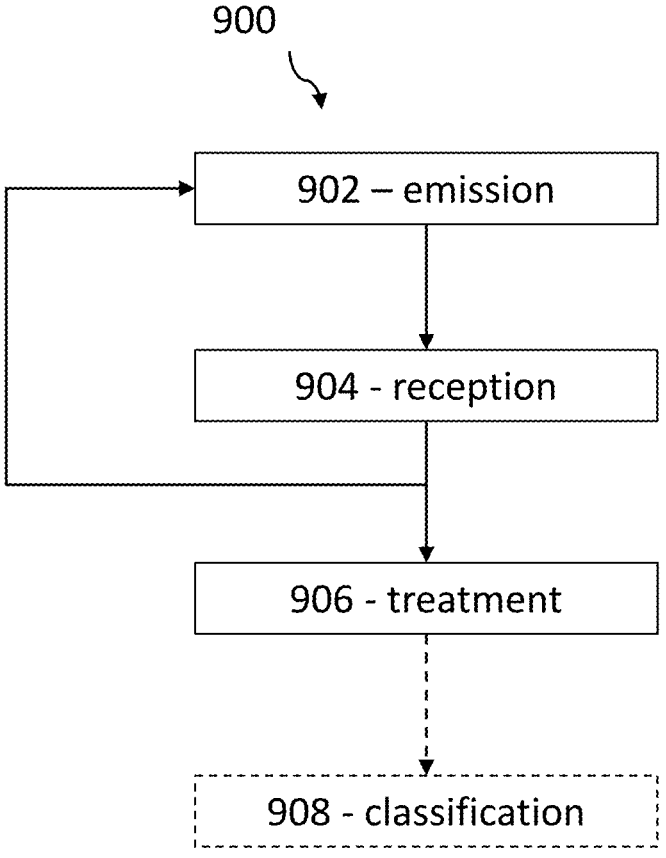
FIG. 9 shows a diagram representing a measurement process according to an embodiment of the invention.

FIG. 9 shows a diagram 900 representing the steps of a measurement method. The steps of method 900 may be implemented by control circuitry 302, 406. In a step 902, the control circuitry drives the radar sensor to emit signals. In a step 904, the control circuitry drives the radar sensor to receive reflected signals. Steps 902, 904 may be repeated several times to create an image. In step 906, the control circuitry processes the reflected signals. Processing examples have been described previously. In particular, the control circuitry calculates at least one property of the urine jet, including velocity (e.g. Vmax), radial distance (e.g. Rmax) and dispersion level (e.g. Npix). In a step 908, the control circuitry uses one or more classification rules stored in the control circuitry to classify the urine jet as coming from a male person or a female person and thus identify the user. In particular, control circuitry 302, 406 classifies the urine stream using at least one property of the urine stream. By identification, it is meant that the control circuitry may assign the urine jet to a given user profile from among a plurality of user profiles stored in the control circuitry 302, 406. In particular, the allocation may be made to a male or female profile depending on the classification. In this embodiment, the control circuitry stores a maximum of one profile for each gender. In an embodiment, the control circuitry stores at most one profile of each gender.

Depending on the classification of step 908, the control circuitry may or may not implement a urine analysis process as described in the aforementioned patent documents. For example, if classification step 908 determines that the urine stream is assigned to a female profile, a urine analysis may be implemented to determine a hormone level related to the menstrual cycle. Conversely, if classification step 908 determines that the urine stream is assigned to a male profile, no urine analysis is initiated. This drastically saves on urinalysis sessions by correctly identifying the person urinating.

The classification step 908 may be performed by the smartphone or server and not by the control circuitry. Similarly, part of processing step 906 may be performed by the smartphone or server. Since user detection may condition the triggering of a measurement, and since urination only lasts a few seconds, it may be important for the classification step to be carried out by the radar device's control circuitry itself. A round trip to the server requires a stable Internet connection and immediate availability of the server. To have an embedded algorithm, clustering without machine learning can be used.

Urine Sensor

In order to trigger radar acquisition only when a urine stream is in progress (to save battery power), the toilet may incorporate a urine detector 210. More specifically, the urine detector is mounted in the radar device 100. The urine detector 210 may detect the presence of a urine stream. Urine detector 210 may include a temperature sensor 220 mounted in housing 200, for example at collection port 204. When urine over 35° C. drips onto the housing, the temperature sensor 220 will detect a sudden rise in temperature.

Figure 10:
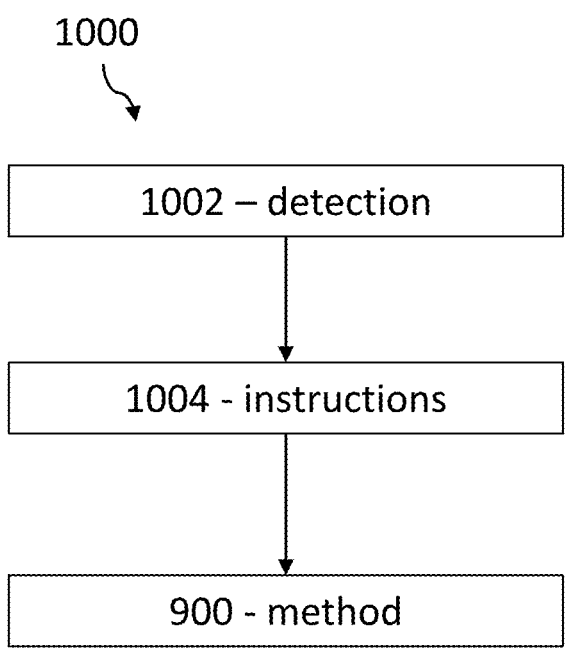
FIG. 10 shows a diagram representing a measurement process according to an embodiment of the invention, with prior detection of urine.

FIG. 10 shows a diagram 1000 representing a method for activating the radar sensor 202. In a step 1002, the urine sensor detects the presence of a stream of urine. In a step 1004, in response to said detection, control circuitry 302, 406 commands radar sensor 202 to perform method 900.

To identify a urine stream parameter, it is not always necessary to obtain a radar image of the entire micturition. In particular, for identification purposes based on the above-mentioned properties of the urine stream, a single radar image of the urine stream may suffice. Missing the start of micturition therefore poses no particular difficulties. The method presented is therefore particularly robust to the temporality of radar sensor activation.

In another embodiment, the urine sensor is replaced by a user presence sensor. This sensor may be a charge cell or an optical sensor. However, such a presence sensor cannot inform the 202 radar sensor that a urine stream is in progress, but only that a user is seated. Consequently, the radar sensor may be expected to send out prospective waves a few seconds before urination occurs to ensure that it acquires radar signals reflected by the urine stream.

Positioning the Radar Sensor in the Toilet

Figure 11:
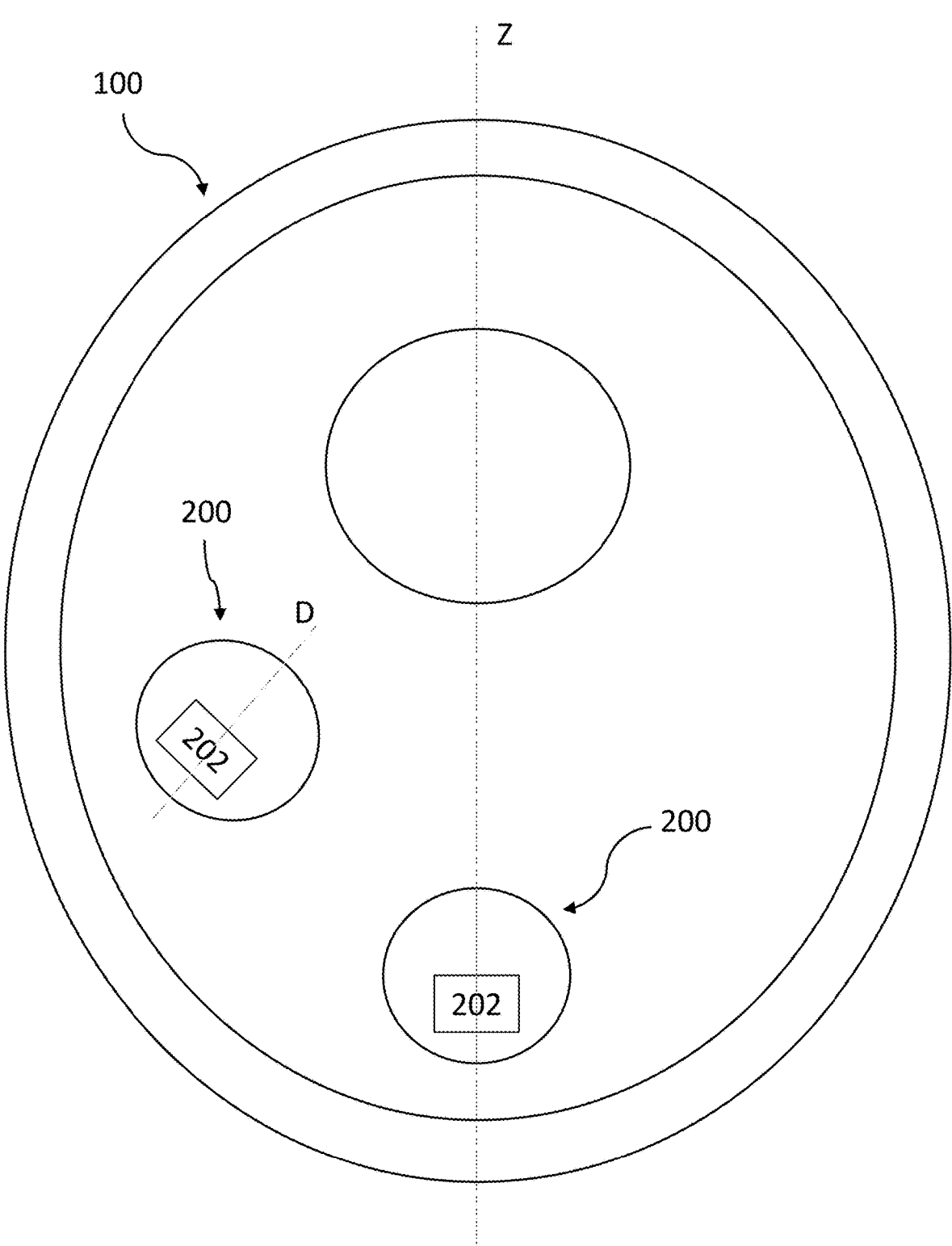
FIG. 11 shows a schematic view of the placement of the radar sensor in the housing and/or in the toilet.

FIG. 11 illustrates various possible locations for the radar device 100 and in particular the radar module 202 inside the housing.

In an embodiment, the radar sensor 202 is centered with respect to an axis of symmetry D of the housing 200; if the user centers the housing 200 on an axis of symmetry Z of the toilet, then the radar sensor 200 is centered with respect to the toilet. This central positioning makes it possible to observe radial speeds that are closer to the actual ejection speed. On the other hand, the risk of not seeing the entire jet increases.

In an embodiment, the radar sensor 202 is off-center with respect to an axis of symmetry of the housing 200; if the user centers the housing 200 on an axis of symmetry Z of the toilet, then the radar sensor 202 is slightly off-center with respect to the toilet. This positioning enables the radar sensor 202 to observe the jet slightly from the side (assuming that, on average, urine jets are made along the axis of symmetry), thus increasing the probability of observing the entire jet and increasing measurement accuracy.

In an embodiment, housing 200 is positioned at a distance from the toilet's axis of symmetry, i.e. slightly offset to the right or left.

In the case of integration of the radar device with a urine analysis device, the housing 200 must be located under the urine stream, which means that the unit must be positioned in the proximal part of the toilet bowl, preferably close to an axis of symmetry Z of the toilet.

Integration of a Radar Sensor in a Urine Analysis Device

In an embodiment, the radar device is integrated into a urine analysis device. The urine device has been described in documents WO2021/175909, WO2021/175944 (publication number), FR2109383, FR2109384, FR2109391, and FR2109392 (application number). The contents of all of these documents are incorporated herein by reference in their entireties. User classification may be a prerequisite for triggering a urinalysis. User classification also enables analysis results to be assigned to the right profile.

Figure 12:
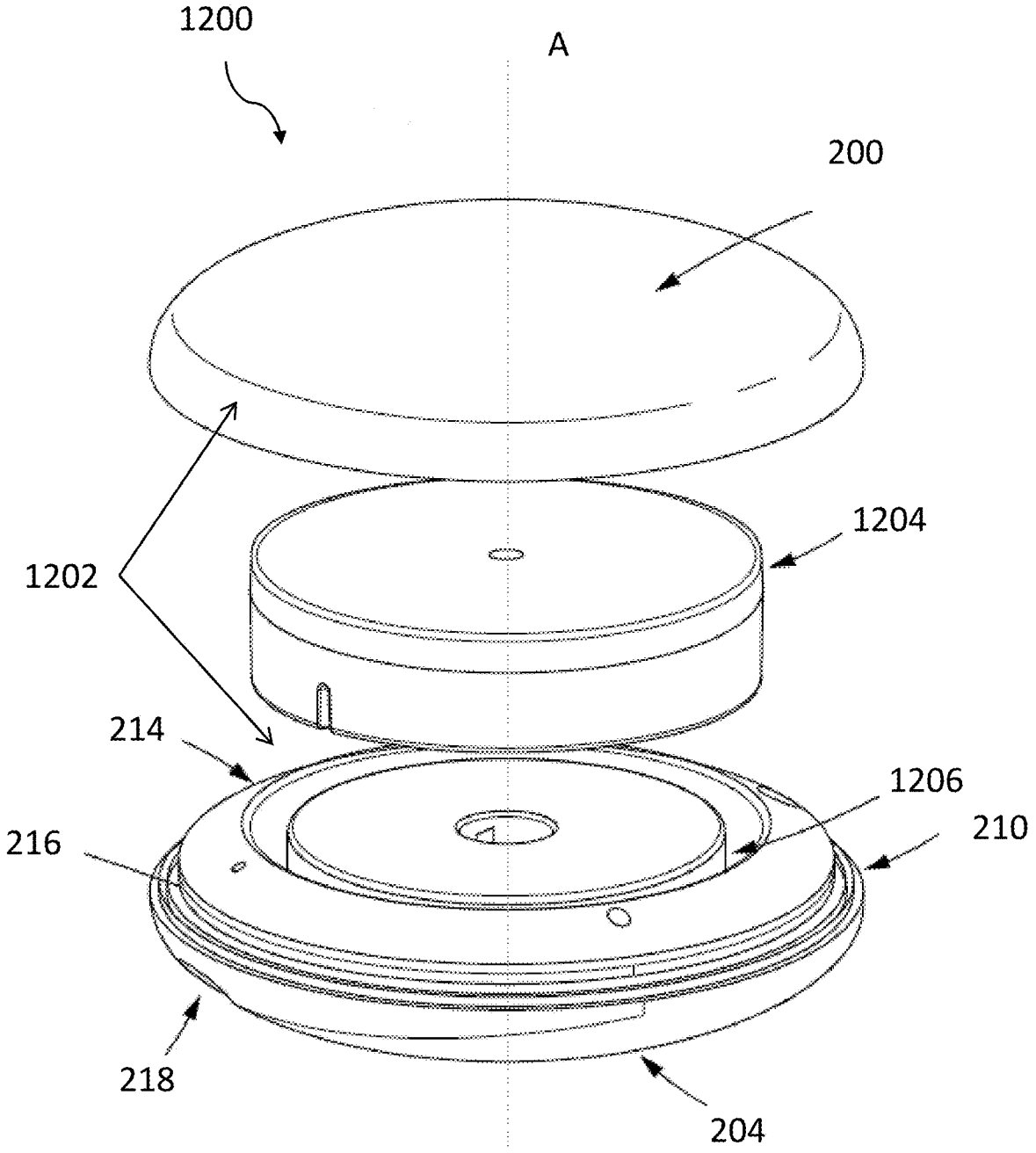
FIG. 12 shows a schematic view of a urine analysis device incorporating the radar device, according to an embodiment of the description.

As illustrated in detail in FIG. 12, the urine analysis device 1200 comprises a station 1202 and a cartridge 1204, removably mounted in station 1202. In particular, station 1202 comprises housing 200 which, according to a particular embodiment, is formed as an assembly of two half-shells. Housing 200 contains a test assembly. The test assembly is designed to analyze the urine received in the urine analysis device 100. Station 1202 further comprises an annular housing 1206, inside housing 200, arranged around a rotation axis A. The annular housing 1206 is configured to at least partially receive the cartridge 1204 mounted for rotation about the axis of rotation A (once in position in the annular housing 212). The cartridge 1204 comprises a plurality of reagent-integrating test supports, for example a dry reagent, arranged along a circle or arc of a circle around the axis of rotation A. In an embodiment and for the remainder of the description, the test carriers are test strips. The test carriers are individually enclosed in a chamber.

The annular housing 1206 typically extends through 360° and forms a groove configured to partially receive the cartridge 1204.

Station 1202 also includes collection port 218, positioned for example on the rear shell in FIG. 12. Collection port 218 may receive urine flowing by gravity over the outer surface of housing 200. A drain port (not shown) is also included to evacuate liquid from the device 1200.

In an embodiment, housing 200 has a diameter, measured in the direction normal to axis A, of between 50 mm and 150 mm, for example close to 100 mm.

The test assembly comprises a pump, an injector and an analyzer, not visible in FIG. 12. The pump draws urine from the collection port 218 and then the injector injects the urine onto a test carrier of the cartridge, then the analyzer obtains properties of the test carrier after it has contacted the urine. The injector and cartridge may move relative to each other so that the injector may pierce the chamber.

It will be appreciated that the various embodiments and aspects of the inventions described previously are combinable according to any technically permissible combinations.

The articles "a" and "an" may be employed in connection with various elements and components, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

The invention claimed is:

1. A measurement method of a urine stream of a user during urination to identify a user, the measuring method using a radar sensor and comprising:

emitting, by the radar sensor, at least one radar signal in a direction of the urine stream, receiving, by the radar sensor, a reflected radar signal, the received radar signal comprising reflections of the emitted signal, the reflections being caused by at least the urine stream, processing, the received radar signal, to determine at least one property relating to the urine stream, said at least one property determined by said processing including a dispersion level of the urine stream and at least one of (i) a distance between the origin of a urine front of the urine stream and the radar sensor and (ii) a maximum measured velocity of the urine stream, and assigning the urine stream to a user profile on the basis of the at least one property of the urine stream.

2. The measurement method according to claim 1, wherein said distance is obtained by:

identifying a radial velocity of interest related to a maximum radial velocity of the urine front of the urine stream, and obtaining a radial distance corresponding to said radial velocity of interest, said radial distance corresponding to the distance.

3. The measurement method according to claim 1, wherein said dispersion level is obtained by calculating a reflection level of the reflected radar signals.

4. The measurement method according to claim 1, wherein the assigning comprises an assignment between a user profile associated with a male and a user profile associated with a female.

5. The measurement method according to claim 4, wherein the assignment is made by classification on the basis of at least one property relating to the urine stream and a classification function.

6. The measurement method according to claim 1, wherein the radar sensor operates per frame, each frame being generated by a plurality of chirps, and transmission and reception steps being carried out for each chirp.

7. The measurement method according to claim 1, wherein the radar sensor is a Frequency Modulated Continuous Wave, FMCW, radar sensor, or the radar signal is FMCW.

8. The measurement method according to claim 1, wherein the signal processing comprises calculation of at least one range-doppler response.

9. The measurement method according to claim 1, further comprising a prior step, using a urine detector, of determining the presence of a urine stream, the method comprising, in response to said detection, a step of activating the radar sensor.

10. A non-transitory computer-readable medium including a computer program comprising instructions to implement a measurement method according to claim 1 when the instructions are executed by a processor.

11. A radar device comprising:

a housing adapted to be positioned on an internal wall of a toilet bowl, a radar sensor, housed in the housing, and adapted to emit radar waves in a direction of the toilet bowl opening, the radar sensor being adapted to implement the method according to claim 1.

12. The radar device according to claim 11, wherein radar sensor is a Frequency Modulated Continuous Wave, FMCW, radar sensor.

13. The radar device according to claim 11, comprising a urine detector adapted to detect a stream of urine, the urine detector being configured to activate the radar sensor in response to a detection of the stream of urine.

14. A urine analysis device, comprising:

a radar device according to claim 11, a collection port on the housing for receiving urine, a test set for analyzing the urine received.

15. The measurement method according to claim 1, wherein the processing comprises determining from the received radar signal said dispersion level of the urine stream, said distance between the origin of the urine front of the urine stream and the radar sensor, and said maximum measured velocity of the urine stream.

16. The measurement method according to claim 1, wherein the at least one property is determined based only on the received radar signal.

17. A measurement method of a urine stream of a user during urination to identify a user, the measuring method using a radar sensor and comprising:

emitting, by the radar sensor, at least one radar signal in a direction of the urine stream, receiving, by the radar sensor, a reflected radar signal, the received radar signal comprising reflections of the emitted signal, the reflections being caused by at least the urine stream, processing, the received radar signal, to determine at least one property relating to the urine stream, said at least one property including one or more of (i) a distance between an origin of a urine front of the urine stream and the radar sensor, (ii) a maximum measured velocity of the urine stream and (iii) a dispersion level of the urine stream, and assigning the urine stream to a user profile on the basis of the at least one property of the urine stream, wherein the radar sensor is included in a urine analysis device having a front surface and a back surface, the back surface adapted to be positioned against an internal wall of a toilet bowl, the urine analysis device comprising a urine collection orifice provided on the back surface.

18. A radar device comprising:

a housing adapted to be positioned on an internal wall of a toilet bowl, a radar sensor, housed in the housing, and adapted to emit radar waves in a direction of the toilet bowl opening, the radar sensor being adapted to implement the method according to claim 17.

19. A urine analysis device, comprising:

a radar device according to claim 18, a collection port on the housing for receiving urine, a test set for analyzing the urine received.

* * * * *